United States Patent [19]

Wevers et al.

[11] Patent Number: 5,021,061
[45] Date of Patent: Jun. 4, 1991

[54] PROSTHETIC PATELLO-FEMORAL JOINT

[75] Inventors: Henk W. Wevers, Glenburnie; John F. Rudan, Kingston, both of Canada

[73] Assignee: Queen's University at Kingston, Kingston, Canada

[21] Appl. No.: 588,263

[22] Filed: Sep. 26, 1990

[51] Int. Cl.⁵ ............................................. A61F 2/38
[52] U.S. Cl. ...................................... 623/20; 623/16
[58] Field of Search ........................... 623/20, 18, 16

[56] References Cited

U.S. PATENT DOCUMENTS

| | | | |
|---|---|---|---|
| 3,806,961 | 4/1974 | Müller | 623/20 |
| 3,964,106 | 6/1976 | Hutter, Jr. et al. | 623/20 |
| 4,094,017 | 6/1978 | Matthews et al. | 623/20 |
| 4,151,615 | 5/1979 | Hall | 623/20 |
| 4,158,894 | 6/1979 | Worrell | 623/20 |
| 4,215,439 | 8/1980 | Gold et al. | 623/20 |
| 4,769,040 | 9/1988 | Wevers | 623/20 |
| 4,944,756 | 7/1990 | Kenna | 623/20 |

Primary Examiner—Ronald Frinks
Attorney, Agent, or Firm—Richard J. Hicks

[57] ABSTRACT

A thin plate patello-femoral-tibial resurfacing prosthesis is described. The patellar component is a metallic shell which is designed to be as thin as possible so as to retain maximum natural bone thickness and hence strength. The metallic patellar component articulates with a plastic insert in a metallic femoral component. The tibial bearing area of the femoral component is metallic for articulation with a plastic proximal tibial prosthesis.

9 Claims, 1 Drawing Sheet

PROSTHETIC PATELLO-FEMORAL JOINT

FIELD OF INVENTION

This invention relates to a patello-femoral-tibial joint prosthesis and more particularly to a novel composite femoral prosthesis.

BACKGROUND OF INVENTION

Knee prostheses have been successfully implanted in older patients suffering from arthritis. Older patients are defined as persons approximately 65 years and over. Generally, a knee prosthesis comprises three components: the kneecap or patella, the lower end of the thigh bone or distal femur, and the upper end of the shin bone or proximal tibia. In current knee prostheses the patella is usually a plastic dome of ultra-high molecular weight polyethylene (UHMWPE) with or without a metal backing. A total prosthetic patella is generally impractical due to the impossibility of attaching viable ligaments thereto. The femur is without exception, made of a solid biocompatible metal alloy (such as cobalt chromium alloy, stainless steel or titanium alloy), and the proximal tibial prosthesis is made of UHMWPE with or without a metal backing.

In older sedate patients the existing prostheses may relieve arthritic pain and restore motion to a large extent, although some problems such as loosening of the prosthesis from the bone, poor or improper tracking of the patella, less than full normal extension and flexion and breakdown of materials may exist. When, however, the existing implants are used for younger patients, who may be heavyset or who are physically active or engaged in heavy work, problems arise, such as premature rapid wear of the UHMWPE and breakage of the remaining patellar bone in addition to the above-mentioned problems. Breakage of the patellar bone is particularly important and is caused by removing much bone and fibrous tissue from the natural patella to accommodate the usual 8- to 10-mm thick, often domed, patellar prostheses, weakening the natural patella by as much as 80% of its original strength. Furthermore, the patella is a relatively small component, compared to the tibia and femoral condyles, and yet the traction forces on the patella can be as high as 1800 lbs (800 N) and the contact forces can reach similar levels. These forces are between 3 and 10 times body weight and the current patellar prostheses have not been designed to accommodate these higher forces in physically active persons. The breakage aforementioned, plus premature wear and fatigue failure of the UHMWPE and the metal backing may thus become acute.

OBJECT OF INVENTION

It is, therefore, an object of the present invention to provide a patello-femoral prosthesis which requires minimal bone removal from the patella, thus maximizing the remaining bone strength.

It is another object of the invention to provide a composite resurfacing femoral prosthesis for articulation with a metallic patellar prosthesis and a non-metallic tibial prosthesis.

BRIEF STATEMENT OF INVENTION

By one aspect of this invention there is provided a knee joint prosthesis comprising a patellar component and a femoral component; said patellar component comprising a thin shell having a shaped anterior surface adapted to be secured within a resected patella of a patient, and a convex posterior surface adapted to articulate within a resected femur of said patient between opposed condyles thereof; the femoral component including a metal shell having a shaped posterior surface portion between opposed condyles adapted to be secured within said resected femur, and a concave anterior surface adapted to receive and retain an element of dissimilar material to said thin shell having a mating convex posterior surface and a concave anterior surface for articulation with said convex posterior surface of said patellar component.

By another aspect of this invention there is provided a knee joint prosthesis comprising a femoral resurfacing metallic component having a first bearing surface arranged for articulation with a tibial prosthesis of dissimilar material and a second bearing surface arranged for articulation with a metallic patellar prosthesis, said second bearing surface being formed by a dissimilar material set into said femoral component.

DETAILED DESCRIPTION OF PREFERRED EMBODIMENTS

Figure 1:
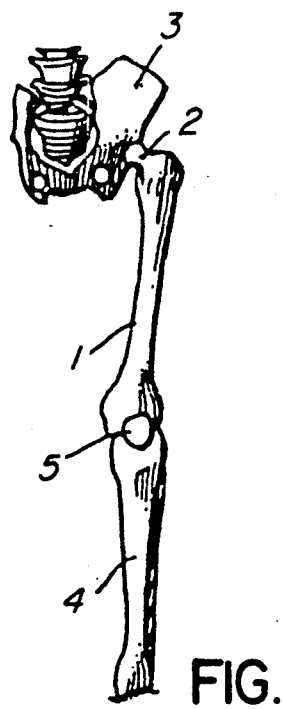
FIG. 1 is a front elevational view of a human femur, patella and tibia.
Figure 2:
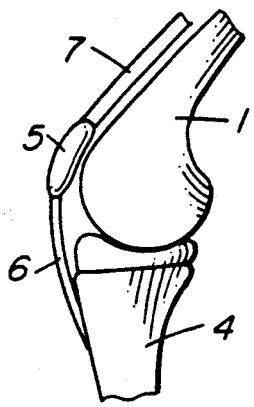
FIG. 2 is a schematic side view of the femur, patella and tibia showing the direction of pull on the patella during extension of the tibia.
Figure 3:
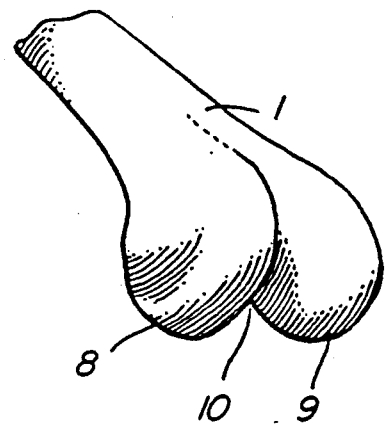
FIG. 3 is a perspective view of the distal end of the femur.
Figure 4:
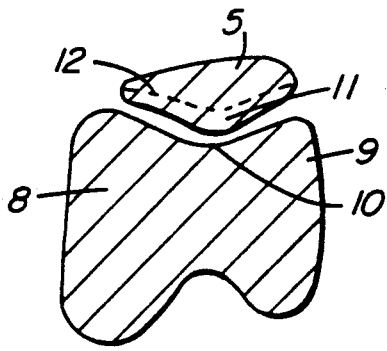
FIG. 4 is a transverse sectional view through the femur showing the relationship between the patella and the femur.
Figure 5:
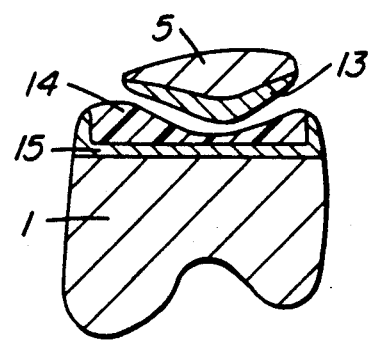
FIG. 5 is a sectional view through the femur showing patellar and femoral prostheses secured to the resected patella and femur.
Figure 7:
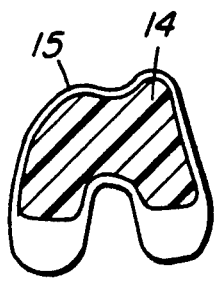

FIGS. 1 and 2 illustrate the spatial relationships between the femur, patella and tibia in a human being. The femur 1 has a ball-like proximal end to which seats laterally in a socket of pelvis 3, and extends downwardly and medially from the pelvis. The distal end of femur 1 is supported on the proximal end of tibia 4 which in turn extends vertically downwardly therefrom. The patella 5 is connected to the tibia 4 by the patella ligament 6, and the tibia 4 is extended from the flexed position shown in FIG. 2 by a pulling force exerted by the quadriceps muscle group 7. FIG. 3 shows the distal end of femur 1 and includes the cam-shaped condyles 8, 9 and an intercondylar groove 10 which extends between the condyles in both the anterior and distal aspects. The groove 10 provides a generally concave surface which receives the convex projection 11 on the patella (FIG. 4). The intercondylar groove stabilizes the patella and prevents medial and lateral displacement thereof as it moves in response to the flexing and extending forces of the quadriceps muscle group 7. As previously noted, these forces are considerable and the patella is a relatively small component to transmit these forces. Further, as the patella is, effectively, a "floating" bone held in place only by the ligaments attached thereto it is generally not possible to remove the patella and replace it with a total patellar prosthesis as there would be nothing viable to secure the ligaments to. The ligaments themselves are, of course, too short to be interconnected over a metal prosthesis and still provide movement in the knee. If the patella is so damaged or worn that it cannot be resurfaced then it is necessary to remove it altogether and secure the ends of the ligaments together. The amount of patella to be resected is, therefore, a critical factor in view of the loads applied and it is an aim of the present invention to remove as little bone as possible so that the resected patella and prosthesis return at least 80% of the natural patella strength. The portion of the patella 5 which is resected is shown by the dotted line 12 in FIG. 4. Removal of such small amounts of bone dictates that the resurfacing prosthesis 13 inserted must be fabricated from a material having very high bearing strength and it has been found that the reinforced UHMWPE previously employed is not strong enough. It is, therefore, preferred to use a metal, such as a cobalt chromium alloy (sold under the trademark Vitallium) stainless steel, or titanium alloy, for resurfacing prosthetic patella 13. Ceramic or other suitable bio-compatible materials are also contemplated. It is, of course, axiomatic that the surface 14 of the femoral prosthesis which mates with the patellar prosthesis 13 must be of dissimilar material and conventional or reinforced UHMWPE is preferred. The shape of the femoral/patella mating surfaces is shown in FIGS. 5 and 7. The UHMWPE part 14 of the femoral prosthesis is contained within a metal resurfacing femoral component 15, to be described in more detail hereinafter.

Figure 6:
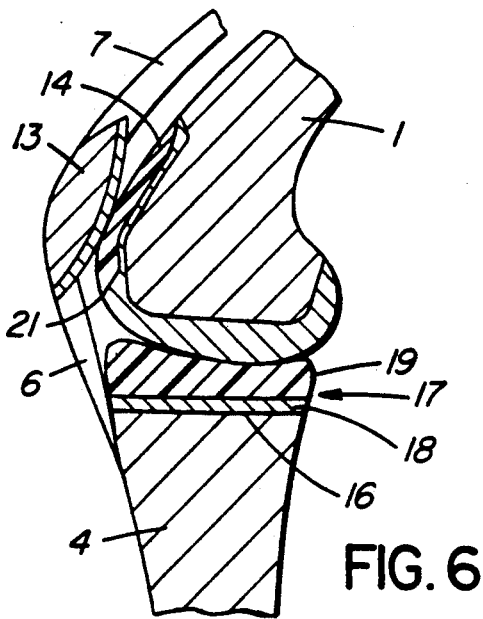
FIG. 6 is a schematic side sectional view of the femur, patella and tibia showing femoral, patellar and tibial prostheses secured to the resected femur and tibia; and, FIG. 7 is a plan view of the femoral prosthesis on the longitudinal axis thereof.

Turning now to the tibia 4, the proximal end 16 of which is resected to receive a somewhat flexible tibial plateau 17 such as that described in more detail in U.S. Pat. No. 4,769,040 assigned to the assignee of the present application. The tibial plateau includes a flexible metal baseplate 18 having a substantially continuous hoop which surrounds the resected end of tibia 4, as seen in FIG. 6. Contained within the metal baseplate is a high density polyethylene (UHMWPE) bearing pad 19, contoured to receive the tibial bearing surface 20 of the femoral component 15. As the bearing pad 19 must be made of a plastics material in order to achieve the desired flexibility, it is apparent that the bearing surface 20 of the femoral component 15 must be made of a dissimilar material, preferably a metallic material. Thus, the femoral component 15 is a composite structure, having a metallic shell and tibial bearing surface 15, with a patello bearing surface 14 comprising an UHMWPE pad insert 14. The boundary 21 between the UHMWPE patello femoral section 14 and the rest of the femoral component 15 does not interfere with either the patellar prosthesis 13 nor the tibial prosthesis 19, except possibly at extreme flexion (130-140 degrees) which is not normally achieved by patients who have undergone resurfacing arthroplasty.

In order to achieve the best possible mechanical properties, including fatigue properties, stiffness and mechanical strength, it is preferred, but not essential, that the UHMWPE femoral pad 14 and the tibial pad 19 should be reinforced with a titanium wire mesh backing which is sold under the trademark Sulmesh by Sulzer Brothers of Switzerland.

We claim:

1. A knee joint prosthesis comprising a patellar component and a femoral component; said patellar component comprising a thin metallic shell having a shaped anterior surface adapted to be secured within a resected patella of a patient, and a convex posterior surface adapted to articulate within a resected femur of said patient between opposed condyles thereof; the femoral component including a metal shell having a shaped posterior surface portion between opposed condyles adapted to be secured within said resected femur and a concave anterior surface adapted to receive and retain an element of dissimilar material to said thin shell having a mating convex posterior surface and a concave anterior surface for articulation with said convex posterior surface of said patellar component.

2. A knee joint prosthesis as claimed in claim 1 wherein said metallic femoral component includes a convex tibial bearing surface adjacent but separated from said patella-articulating element articulating with said convex posterior surface of said patellar component.

3. A knee joint prosthesis comprising a patellar component, a femoral component and a tibial component; said patellar component comprising a thin shell having a shaped anterior surface adapted to be secured within a resected patella of a patient, and a convex posterior surface adapted to articulate within a resected femur of said patient between opposed condyles thereof; said femoral component including a metal shell having a shaped posterior surface portion between opposed condyles adapted to be secured within said resected femur and a concave anterior surface adapted to receive and retain an element of dissimilar material to said thin shell having a mating convex posterior surface and a concave anterior surface for articulation with said convex posterior surface of said patellar component; and wherein said femoral component includes a concave posterior surface adapted to be secured on a convexly resected distal end of said femur and a convex anterior surface for articulation with said tibial component; and wherein said tibial component includes a contoured pad of dissimilar material for articulation with said convex anterior surface of said femoral component.

4. A knee joint prosthesis as claimed in claim 3 wherein said contoured pad in said tibial component is an ultra high molecular weight polyethylene pad.

5. A knee joint prosthesis as claimed in claim 4 wherein said contoured pad is contained within a metallic shell sized to conform, in cross section, to the proximal end of a resected tibia.

6. A knee joint prosthesis as claimed in claim 1 wherein said thin shell of said patellar component is a metallic shell sized such that said resected patella retains at least 80% of its natural strength.

7. A knee joint prosthesis as claimed in claim 3 wherein said thin shell of said patellar component is a metallic shell sized such that said resected patella retains at least 80% of its natural strength.

8. A knee joint prosthesis comprising a femoral resurfacing metallic component having a first bearing surface arranged for articulation with a tibial prosthesis of dissimilar materials and a second bearing surface arranged for articulation with a patellar prosthesis, said second bearing surface being formed by a dissimilar material set into said femoral component.

9. A knee joint prosthesis as claimed in claim 8 wherein said second bearing surface comprises an ultra high molecular weight polyethylene pad mounted in said metallic femoral component.

* * * * *